United States Patent
Jung et al.

(10) Patent No.: US 12,427,096 B2
(45) Date of Patent: Sep. 30, 2025

(54) COSMETIC COMPOSITION FOR SUSTAINING LUSTER

(71) Applicant: LG Household & Health Care Ltd., Seoul (KR)

(72) Inventors: Eun-Ji Jung, Seoul (KR); Eun-Ji Jung, Gyeonggi-do (KR); Sung-Soo Kang, Seoul (KR)

(73) Assignee: LG Household & Health Care Ltd., Seoul (KR)

( * ) Notice: Subject to any disclaimer, the term of this patent is extended or adjusted under 35 U.S.C. 154(b) by 798 days.

(21) Appl. No.: 17/290,499

(22) PCT Filed: Oct. 22, 2019

(86) PCT No.: PCT/KR2019/013904
§ 371 (c)(1),
(2) Date: Apr. 30, 2021

(87) PCT Pub. No.: WO2020/091287
PCT Pub. Date: May 7, 2020

(65) Prior Publication Data
US 2022/0000728 A1 Jan. 6, 2022

(30) Foreign Application Priority Data

Nov. 1, 2018 (KR) ........................ 10-2018-0133182
Jun. 25, 2019 (KR) ........................ 10-2019-0075951

(51) Int. Cl.
| | |
|---|---|
| *A61K 8/06* | (2006.01) |
| *A61K 8/34* | (2006.01) |
| *A61K 8/81* | (2006.01) |
| *A61K 8/89* | (2006.01) |
| *A61Q 1/02* | (2006.01) |

(52) U.S. Cl.
CPC .............. *A61K 8/064* (2013.01); *A61K 8/345* (2013.01); *A61K 8/8141* (2013.01); *A61K 8/89* (2013.01); *A61Q 1/02* (2013.01)

(58) Field of Classification Search
CPC ...... A61K 8/064; A61K 8/345; A61K 8/8141; A61K 8/89; A61K 8/37; A61K 8/375; A61K 8/8152; A61K 8/585; A61K 8/891; A61K 8/92; A61Q 1/02; A61Q 1/04; A61Q 1/00
See application file for complete search history.

(56) References Cited

U.S. PATENT DOCUMENTS

| | | | | |
|---|---|---|---|---|
| 5,817,298 | A * | 10/1998 | Galley | B82Y 30/00 424/59 |
| 6,379,682 | B1 * | 4/2002 | Tchinnis | A61K 8/585 524/588 |
| 2011/0104222 | A1 | 5/2011 | Iida et al. | |
| 2013/0345315 | A1 | 12/2013 | Chiou | |
| 2013/0345316 | A1 | 12/2013 | Chiou | |
| 2015/0359734 | A1 * | 12/2015 | Boland | A61Q 19/02 424/59 |
| 2016/0045422 | A1 | 2/2016 | Huang et al. | |
| 2017/0172903 | A1 | 6/2017 | El Akkari et al. | |
| 2018/0028416 | A1 | 2/2018 | Fu et al. | |

FOREIGN PATENT DOCUMENTS

| | | |
|---|---|---|
| CN | 104519857 A | 4/2015 |
| CN | 107625653 A | 1/2018 |
| CN | 107920963 A | 4/2018 |
| CN | 108324595 A | 7/2018 |
| JP | 2009-173653 A | 8/2009 |
| JP | 201018612 A | 1/2010 |
| JP | 2012-224560 A | 11/2012 |
| JP | 2013107851 A | 6/2013 |
| JP | 2016-124806 A | 7/2016 |
| JP | 2018203624 A | 12/2018 |
| KR | 20140026056 A | 3/2014 |
| KR | 20150017731 A | 2/2015 |
| KR | 20150040864 A | 4/2015 |
| KR | 20160137907 A | 12/2016 |
| WO | 2018221174 A1 | 12/2018 |

OTHER PUBLICATIONS

Schaefer (Trimethylsiloxysilicate Film-Formers for Hair/Skin Feel, Sep. 6, 2011) (Year: 2011).*
Cosmetics and Skin (Glycerine Creams and Jellies, Mar. 24, 2014) (Year: 2014).*
International Search Report for Application No. PCT/KR2019/013904, dated Jan. 28, 2020, 2 pages.
Catalog "Cosmetic Silicone Original Ingredients plus", Shin-Etsu Chemical Co., Ltd., Mar. 2022, pp. 1-23, URL, https://www.silicone.jp/catalog/pdf/pc_original_j.pdf [Brief Summary of translation attached].
Catalog "Personal Care Catalog Cosmetic Specialty Silicone Product Catalog", Momentive Performance Materials, Jun. 2005, p. 16-17, URL, http://www.esung.asia/brochure/pc.pdf [Brief Summary of translation attached].

* cited by examiner

*Primary Examiner* — Frederick F Krass
*Assistant Examiner* — Abdulrahman Abbas
(74) *Attorney, Agent, or Firm* — Saraswati Desai

(57) ABSTRACT

The present disclosure relates to a gloss-sustainable cosmetic composition, which improves a stuffy feel of use, while including a high-refractive index oil, and provides improved skin gloss sustainability. The water-in-oil type cosmetic composition shows a reduced stuffy feel of use caused by high-refractive index oil, and provides significantly high initial gloss and gloss sustainability.

2 Claims, 5 Drawing Sheets

COSMETIC COMPOSITION FOR SUSTAINING LUSTER

CROSS-REFERENCE TO RELATED APPLICATIONS

The present application is a national phase entry under 35 U.S.C. § 371 of International Application No. PCT/KR2019/013904, filed Oct. 22, 2019, which claims priority to Korean Patent Application No. 10-2018-0133182, filed Nov. 1, 2018 and Korean Patent Application No. 10-2019-0075951, filed Jun. 25, 2019 in the Republic of Korea, the disclosures of which are incorporated herein by reference.

TECHNICAL FIELD

The present disclosure relates to a cosmetic composition which can provide improved skin gloss sustainability.

BACKGROUND ART

In general, emulsions used for cosmetics, pharmaceuticals, foods, or the like, are classified broadly into two types. One is an oil-in-water type emulsion including oil dispersed in water in the state of particles, and the other is a water-in-oil type emulsion including water dispersed in oil. The water-in-oil type formulation inhibits evaporation of water from the skin, as compared to the oil-in-water type formulation, so that it may deliver water and a skin active material continuously to the skin, and has a wide range of applications including sunscreen products, skin cover products, hand cream, or the like. However, since a water-in-oil type cosmetic composition includes oil as an external phase, it has many advantages in terms of water resistance, makeup sustainability and a skin protection effect, but shows a heavy feel of use and provides a thick makeup film to cause reduction of skin air permeability.

A cosmetic product, such as foundation, which imparts gloss in base makeup, has been increasingly in demand, and particularly, various skin gloss-imparting products for dry seasons have been launched. When developing a high-gloss formulation for realizing glossy skin with a water-in-oil type base makeup formulation, oil having a high refractive index has been used. However, since such oil having a high refractive index characteristically shows a heavy and thick feel of use, application of various ingredients to the formulation using such oil causes formation of a thick makeup film and provides a stuffy feel of use. In addition, in the case of high-refractive index oil, it is liable to sebum, or the like, to cause easy collapse of a makeup film, and shows reduction of the gloss of the skin to which the formulation is applied, after the lapse of time. An oil phase polymer may be added to a composition including such high-refractive index oil as a main ingredient to prevent collapse of makeup, but application of an oil phase polymer is limited due to the thickness of a makeup film, feel of use, a cosmetic effect, or the like.

DISCLOSURE

Technical Problem

The present disclosure is designed to solve the problems of the related art, and therefore the present disclosure is directed to providing a cosmetic composition which reduces a stuffy feel of use caused by high-refractive index oil, while providing improved skin gloss stainability.

Technical Solution

The present inventors have conducted intensive studies to overcome the above-mentioned problems occurring in the related art, and have found that a water-in-oil type cosmetic composition including high-refractive index oil in combination with a high-refractive index polyol in its internal phase forms a moisturizing layer from the polyol in the internal phase, even after a makeup film collapses after the lapse of time, and shows significantly increased gloss sustainability. In addition, the present inventors have found that when an oil phase polymer is further used for the water-in-oil type formulation, it is possible to realize high initial gloss and to increase gloss sustainability significantly even after the lapse of time. The present disclosure is based on these findings.

In one aspect of the present disclosure, there is provided a water-in-oil type cosmetic composition including a high-refractive index oil and a high-refractive index polyol, wherein the high-refractive index polyol is present in an internal phase. According to an embodiment, the composition may further include an oil phase polymer.

According to an embodiment, the high-refractive index oil may have a refractive index (RI) of 1.39 or more, particularly 1.39-1.6, more particularly 1.4-1.58, and most particularly 1.41-1.56, as determined by the standard test method of ASTM D1218.

The high-refractive index oil may be any oil having a relatively high refractive index with no particular limitation, as long as it is used conventionally for cosmetics. For example, oil having a higher refractive index as compared to the refractive index (1.39) of silicone oil used generally for a water-in-oil type cosmetic product may be used in order to improve the initial gloss and gloss sustainability of the cosmetic composition. According to an embodiment, the high-refractive index oil may include at least one selected from the group consisting of phenyl trimethicone (1.46), diphenylsiloxyphenyl trimethicone (1.50), triethylhexanoin (1.44), dipentaerythrityl hexaC5-9 acid ester (1.52), diisostearyl maleate (1.46), polyglyceryl-2-triisostearate (1.466), or the like, but is not limited thereto. According to a particular embodiment, the high-refractive index oil may include silicone oil, such as phenyl trimethicone, diphenylsiloxyphenyl trimethicone, or a combination thereof. In this case, the cosmetic composition shows significantly improved initial gloss and gloss sustainability.

According to an embodiment, the high-refractive index oil may be used in an amount of 20 wt % or less, such as 1-20 wt %, particularly 1.5-18 wt %, and more particularly 2-15 wt %, based on the total weight of the composition. When the high-refractive index oil is used in an amount of less than 1 wt % based on the total weight of the composition, initial gloss and gloss sustainability may be reduced. When the high-refractive index oil is used in an amount of larger than 20 wt %, a stuffy feel of use or collapse of a makeup film may occur. With a view to reduction of a stuffy feel of used caused by high-refractive index oil, the high-refractive index oil may be blended in an amount of 1-12 wt %, particularly 2-10 wt %, more particularly 3-8 wt %, and most particularly 5-8 wt %, based on the total weight of the composition.

According to an embodiment, the oil phase polymer is an oil phase ingredient capable of enhancing the initial gloss and gloss sustainability of the cosmetic composition, and may be an ingredient having a film-forming property and making a makeup film smooth. The oil phase polymer may include at least one selected from the group consisting of:

silicone resin, such as trimethylsiloxy silicate, phenylpropyldimethylsiloxy silicate, trimethylsiloxy silicate/dimethicone crosspolymer, dimethicone/vinyltrimethyl siloxysilicate crosspolymer, polyphenylsilsesquioxane, polypropylsilsesquioxane, dimethicone/silsesquioxane copolymer, or the like; and acrylate polymer, such as acrylate/stearyl acrylate/dimethicone methacrylate copolymer, acrylate copolymer, acrylate/methacrylate copolymer, acrylate/acrylamide copolymer, acrylate/dimethicone copolymer, acrylate/dimethicone methacrylate copolymer, acrylate/ethylhexyl acrylate copolymer, acrylate/polytrimethylsiloxy methacrylate copolymer, acrylate/VP copolymer, VP/hexadecane copolymer, or the like, but is not limited thereto. According to a particular embodiment, the oil phase polymer may include trimethylsiloxy silicate, acrylate/stearyl acrylate/dimethicone methacrylate copolymer or a mixture thereof. In this case, the cosmetic composition shows significantly high initial gloss and gloss sustainability.

According to an embodiment, the oil phase polymer may be used in an amount of 1-15 wt %, particularly 2-12 wt %, and more particularly 3-10 wt %, based on the total weight of the composition. When the oil phase polymer is used in an amount of less than 1 wt % based on the total weight of the composition, it is not possible to provide a sufficient effect of forming a makeup film, resulting in reduction of a gloss-imparting effect. When the oil phase polymer is used in an amount of larger than 15 wt %, the formulation stability may be worsened.

According to the present disclosure, the high-refractive index polyol contained in the internal phase of the water-in-oil type cosmetic composition forms a moisturizing layer on the skin upon the collapse of a makeup film to increase the gloss-sustaining effect. According to an embodiment, the high-refractive index polyol may have a refractive index (RI) of 1.39 or more, particularly 1.39-1.6, more particularly 1.4-1.58, and most particularly 1.41-1.56, as determined by the standard test method of ASTM D1218.

According to an embodiment, the high-refractive index polyol may include at least one selected from the group consisting of glycerin (1.47), butylene glycol (1.44), dipropylene glycol (1.44), polyethylene glycol (1.46-1.47), 1,3-propanediol (1.44), 1,2-hexanediol (1.44), pentylene glycol (1.43), or the like, but is not limited thereto. According to a particular embodiment, the high-refractive index polyol may include at least one selected from the group consisting of glycerin, butylene glycol and dipropylene glycol. In this case, it is possible to provide a significantly high gloss-sustaining effect through the formation of a moisturizing film, when a makeup film collapses.

According to an embodiment, the high-refractive index polyol may be used in an amount of 10-20 wt %, particularly 10-18 wt %, and more particularly 10-16 wt %, based on the total weight of the composition. Since the cosmetic composition includes the high-refractive index polyol within the above-defined range of amount, it shows significantly high gloss-sustainability despite the presence of a reduced amount of high-refractive index oil, and thus can solve the problem of a stuffy feel of use caused by the use of a large amount of high-refractive index oil. When the high-refractive index polyol is used in an amount of less than 10 wt % based on the total weight of the composition, gloss-sustainability may be reduced. When the high-refractive index polyol is used in an amount of larger than 20 wt %, the stability of the water-in-oil type formulation may be worsened.

Although it is not intended to be bound to the theory, blending with a large amount of a high-refractive index polyol may impart gloss-sustainability, while reducing a stuffy feel of use caused by the use of a large amount of high-refractive index oil. When high-refractive index oil in an oil film forming an external film upon the skin application imparts gloss and then the external film is removed out, gloss may be imparted by the internal layer of an aqueous phase containing the high-refractive index polyol to provide gloss sustainability. Based on this principle, the cosmetic composition according to the present disclosure uses a reduced amount of high-refractive index oil and an increased content of high-refractive index polyol to impart a similar level of gloss sustainability, while reducing a stuffy feel of use caused by the use of a large amount of high-refractive index oil.

According to an embodiment, the water-in-oil type cosmetic composition may include, as an oil component in its external phase, at least one selected from the group consisting of: ester oil, such as isodecyl neopentanoate, isostearyl isostearate, ethylhexyl benzoate, phenetyl benzoate, PPG-3 benzyl ether myristate, caprylic/capric triglyceride, isopropyl palmitate, isopropyl isostearate, isopropyl myristate, isostearyl isostearate, or the like; hydrocarbon oil, such as hydrogenated polydecene, mineral oil, fluidized paraffin, squalene, isododecane, isohexadecane, or the like; silicone oil, such as cyclopentasiloxane, cyclohexasiloxane, trimethyl pentaphenyltrisiloxane, diphenyl dimethicone, or the like; and natural vegetable oil, such as olive oil, jojoba oil, castor oil, sweet almond oil, avocado oil, grapeseed oil, malt oil, or the like, but is not limited thereto.

According to an embodiment, the cosmetic composition according to the present disclosure may further include various ingredients that may be used as aqueous phase ingredients conventionally in the art. For example, such ingredients may include water, a moisturizing agent, a metal ion chelating agent, an anti-oxidant, a water-soluble medicament, a neutralizing agent, a water-soluble sunscreen agent, a pigment, a preservative, a fragrance, or the like, but is not limited thereto. In addition to the above-mentioned ingredients, the cosmetic composition according to the present disclosure may be further blended with a suitable amount of other ingredients used conventionally for a water-in-oil type cosmetic composition without detracting from the effect of the present disclosure, and may be prepared by the conventional method. Further, the cosmetic composition according to the present disclosure may be provided in the formulation of foundation, solution, ointment for external use on skin, cream, foam, nutrient toner, skin softener, pack, makeup base, essence, sunscreen cream, sun oil, suspension, emulsion, paste, gel, lotion, oil, spray, or the like, but is not limited thereto.

The water-in-oil type cosmetic composition according to the present disclosure may be prepared by various methods known to those skilled in the art. For example, the water-in-oil type cosmetic composition may be prepared by the following method, but is not limited thereto. The method may include the steps of: (S1) agitating and dispersing each of an oil phase ingredient including a high-refractive index oil and an aqueous phase ingredient including a high-refractive index polyol; (S2) mixing the oil phase ingredient with a colorant and carrying out agitation; and (S3) adding the aqueous phase ingredient to the oil phase ingredient and carrying out emulsification. The oil phase ingredient in step (S1) may further include an oil phase polymer. Steps (S1) to (S3) may be carried out at 80° C., and step (S3) may be carried out by using a homomixer.

Advantageous Effects

The water-in-oil type cosmetic composition according to the present disclosure uses a polyol having a high refractive index in its internal phase, and thus can realize a gloss-sustaining effect through the polyol in the internal phase, when a makeup film collapses after the lapse of time.

In addition, the water-in-oil type cosmetic composition according to the present disclosure uses an oil phase polymer, which can make a makeup film smooth, to realize high initial gloss and to provide excellent gloss sustainability.

The water-in-oil type cosmetic composition according to the present disclosure improves the disadvantages of a conventional glossy makeup cosmetic product, such as a stuffy feel of use and reduction of gloss caused by collapse of makeup, and thus can improve the consumer's satisfaction.

BEST MODE

Figure 1:
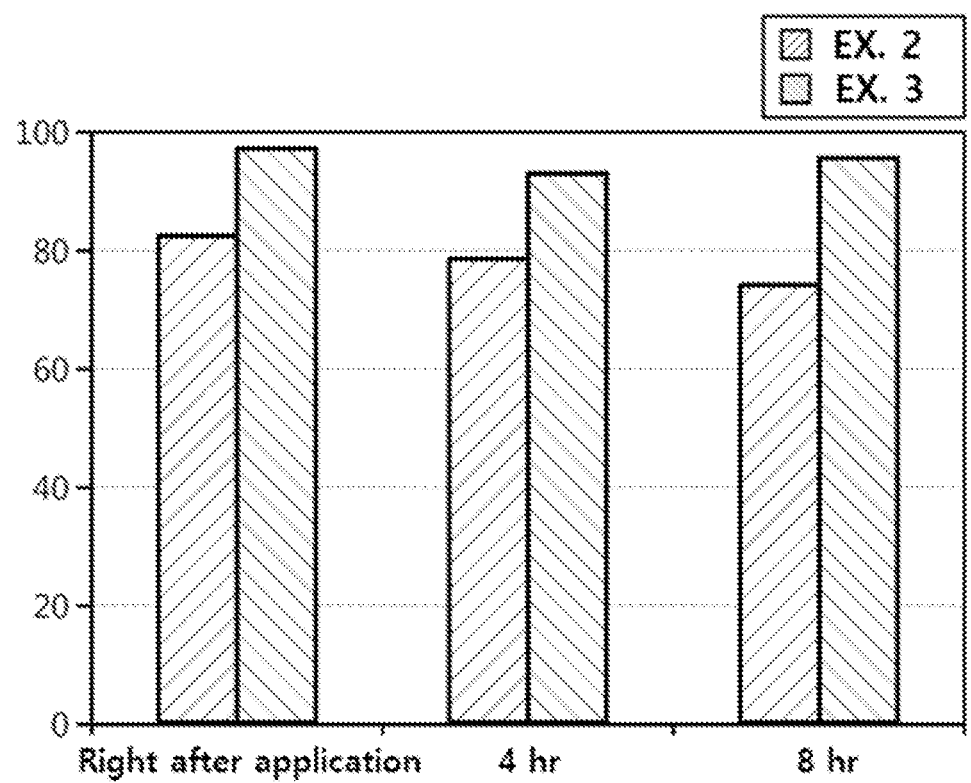
FIG. 1 is a graph illustrating the results of gloss of each of Examples 2 and 3, as determined by using a glossmeter according to Test Example 1.

Examples will be described more fully hereinafter so that the present disclosure can be understood with ease. The following examples may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art.

PREPARATION OF EXAMPLES AND COMPARATIVE EXAMPLES

Water-in-oil type cosmetic compositions were prepared by the following method according to the ingredients and contents (wt %) as shown in the following Table 1.

Preparation Method

1) The oil phase ingredients were mixed, warmed to 80° C. and dispersed.
2) The product of 1) was mixed with the colorants and agitated.
3) In a separate aqueous phase vessel, the aqueous phase ingredients were warmed gradually to 80° C. and dissolved completely.
4) The aqueous phase ingredients of 3) were introduced gradually to the oil phase ingredients of 1), and emulsification was carried out by using a homomixer.
5) After the completion of the emulsification, the resultant product was degassed and cooled to 28° C.

TABLE 1

| | ingredients (wt %) | Comp. Ex. 1 | Comp. Ex. 2 | Comp. Ex. 3 | Comp. Ex. 4 | Comp. Ex. 5 | Ex. 1 | Ex. 2 | Ex. 3 | Ex. 4 | Ex. 5 |
|---|---|---|---|---|---|---|---|---|---|---|---|
| Oil phase ingredients | Cyclopentasiloxane | 15.6 | 5.85 | 2.60 | 15.6 | 15.6 | 15.6 | 5.85 | 2.60 | 5.85 | 9.10 |
| | Cyclohexasiloxane | 8.4 | 3.15 | 1.40 | 8.4 | 8.4 | 8.4 | 3.15 | 1.40 | 3.15 | 4.90 |
| | Phenyltrimethicone | — | 8.00 | 13.00 | — | — | — | 8.00 | 8.00 | 5.00 | 2.00 |
| | Diphenylsiloxy phenyltrimethicone | — | 7.00 | 7.00 | — | — | — | 7.00 | 7.00 | 3.00 | 3.00 |
| | Trimethylsiloxy silicate | — | — | — | — | — | — | — | 5.00 | 5.00 | 5.00 |
| | PEG-10 dimethicone | 3.00 | 3.00 | 3.00 | 3.00 | 3.00 | 3.00 | 3.00 | 3.00 | 3.00 | 3.00 |
| | Disterardimonium hectorite | 1.00 | 1.00 | 1.00 | 1.00 | 1.00 | 1.00 | 1.00 | 1.00 | 1.00 | 1.00 |
| | Fragrance | 0.3 | 0.3 | 0.3 | 0.3 | 0.3 | 0.3 | 0.3 | 0.3 | 0.3 | 0.3 |
| Aqueous phase ingredients | Purified water | Balance | Balance | Balance | Balance | Balance | Balance | Balance | Balance | Balance | Balance |
| | Glycerin | — | — | — | 3.00 | 8.00 | 10.00 | 10.00 | 10.00 | 10.00 | 10.00 |
| | Preservative | Q.S. | Q.S. | Q.S. | Q.S. | Q.S. | Q.S. | Q.S. | Q.S. | Q.S. | Q.S. |
| | Sodium chloride | 0.50 | 0.50 | 0.5 | 0.50 | 0.50 | 0.50 | 0.50 | 0.50 | 0.50 | 0.50 |
| colorants | Titanium dioxide | 10.00 | 10.00 | 10.00 | 10.00 | 10.00 | 10.00 | 10.00 | 10.00 | 10.00 | 10.00 |
| | Yellow iron oxide, Red iron oxide, Black iron oxide | 2.00 | 2.00 | 2.00 | 2.00 | 2.00 | 2.00 | 2.00 | 2.00 | 2.00 | 2.00 |

Test Example 1: Water-In-Oil Type Makeup Cosmetic Formulation Including Oil Phase Polymer To determine the initial gloss and gloss-sustaining effect of a water-in-oil type cosmetic composition including an oil phase polymer which makes a makeup film smooth, Examples and Comparative Examples were tested as follows.

Each of the water-in-oil type makeup cosmetic compositions according to Examples 2 and 3 was tested in terms of gloss. Determination of gloss was carried out by applying each formulation to a thickness of 60 μm on black paper and using a glossmeter (Glossmeter VG 2000, 85°). Gloss was determined right after the application and after the lapse of 4 hours and 8 hours. In addition, gloss determination was carried out three times for each composition, and the initial gloss and a gloss decrease are shown by using the average values. FIG. 1 shows comparison of GU* values obtained through the glossmeter, and Table 2 shows a calculated decrease in gloss (GU*=gloss unit).

TABLE 2

| Decrease in gloss (%) | Example 2 | Example 3 |
| --- | --- | --- |
| 4 hours | 4.96 | 4.43 |
| 8 hours | 10.12 | 1.85 |

As can be seen from the results of FIG. 1 and Table 2, Example 3 using an oil phase polymer shows higher initial gloss as compared to Example 2 including no oil phase polymer. In addition, in terms of a decrease in gloss with the lapse of time, Example 3 shows a significantly lower decrease in gloss with the lapse of time, as compared to Example 2.

Test Example 2: Water-In-Oil Type Makeup Cosmetic Formulation Including Aqueous Phase Polyol To determine the initial gloss and gloss-sustaining effect of a water-in-oil type cosmetic composition using a high-refractive index polyol in the aqueous phase, the formulations according to Examples and Comparative Examples of Table 1 were prepared and tested. The results of gloss determination using a glossmeter for the cosmetic compositions including no high-refractive index oil and using a high-refractive index polyol are shown in FIG. 2, and a decrease in gloss for each cosmetic composition is shown in Table 3.

TABLE 3

| Decrease in gloss (%) | Comp. Ex. 1 | Comp. Ex. 4 | Comp. Ex. 5 | Example 1 |
| --- | --- | --- | --- | --- |
| Decrease (4 hr) | 48.64 | 58.66 | 57.68 | 42.38 |
| Decrease (8 hr) | 68.32 | 77.68 | 69.43 | 55.83 |

Figure 2:
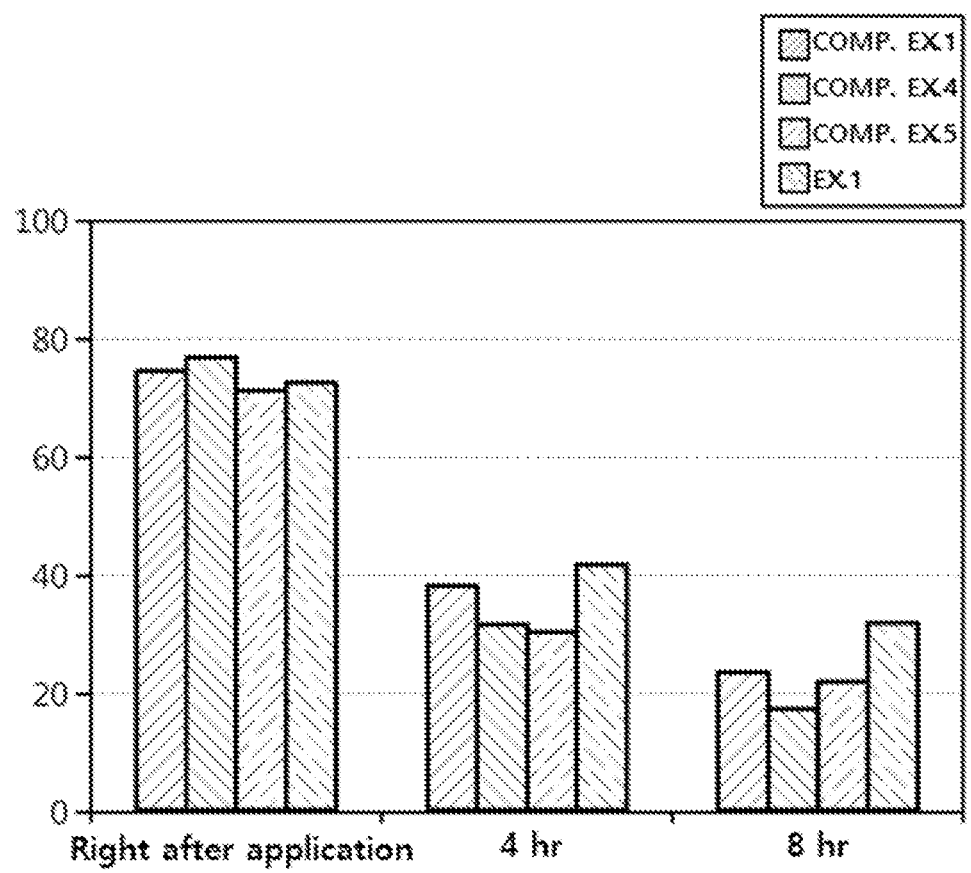
FIG. 2 is a graph illustrating the results of gloss of each of Comparative Examples 1, 4 and 5 and Example 1, as determined by using a glossmeter according to Test Example 2.

As can be seen from the results of FIG. 2 and Table 3, the water-in-oil type makeup cosmetic composition including 10% or more of a high-refractive index polyol in its internal phase (Example 1) shows a significantly lower decrease in gloss as compared to the water-in-oil type makeup cosmetic composition including no high-refractive index oil (Comparative Example 1) and the water-in-oil type makeup cosmetic compositions including a polyol in the internal phase in an amount of less than 10 wt % (Comparative Examples 4 and 5). Therefore, it can be seen that the cosmetic composition according to Example 1 realizes excellent gloss sustainability with the lapse of time.

Figure 3:
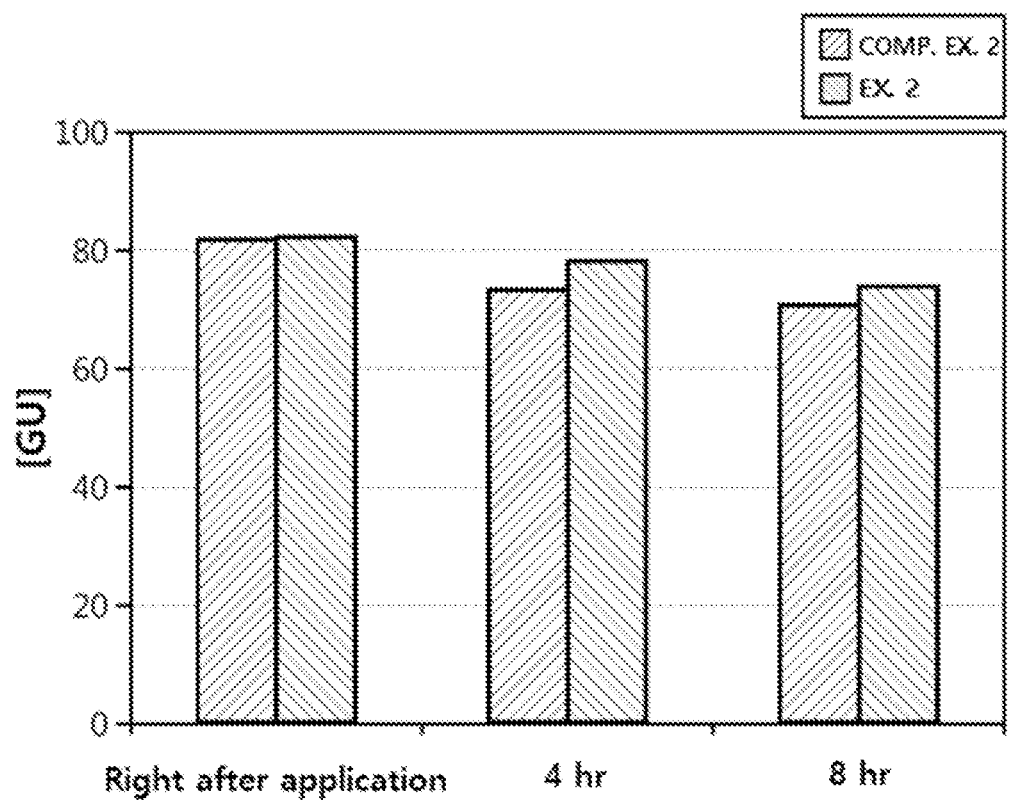
FIG. 3 is a graph illustrating the results of gloss of each of Comparative Example 2 and Example 2, as determined by using a glossmeter according to Test Example 2.

In addition, the results of determination using a glossmeter for the cosmetic compositions including high-refractive index oil in combination with a high-refractive index polyol are shown in FIG. 3, and a decrease in gloss is shown in Table 4.

TABLE 4

| | Comp. Ex. 2 | Example 2 |
| --- | --- | --- |
| Decrease (4 hr) | 10.45 | 4.96 |
| Decrease (8 hr) | 13.61 | 10.12 |

As can be seen from the results of FIG. 3 and Table 4, the water-in-oil type makeup cosmetic composition further including a high-refractive index polyol in its internal phase (Example 2) shows a significant increase in gloss-sustaining effect, as compared to the glossy water-in-oil type makeup cosmetic composition including a large amount of high-refractive index oil (Comparative Example 2). Comparative Example 2 shows a decrease in gloss at a higher rate as compared to Example 2, with the lapse of time, and thus Example 2 shows a significantly lower decrease in gloss and has significantly higher gloss sustainability as compared to Comparative Example 2, after 4 hours or 8 hours.

Test Example 3: Water-In-Oil Type Makeup Cosmetic Formulation Including Large Amount of High-Refractive Index Oil To determine the gloss sustainability and a stuffy feel of use of makeup when using no high-refractive index polyol and merely including a large amount of high-refractive index oil, the following test was carried out. The feel of use was tested by sensory evaluation. Twenty females in their twenties to thirties participated in the test by evaluating sustainability and stuffy feel. Each test panel was allowed to give a score from 0 to 5, the scores were averaged, and the result is shown as the average value (a higher value shows a better result).

Figure 4:
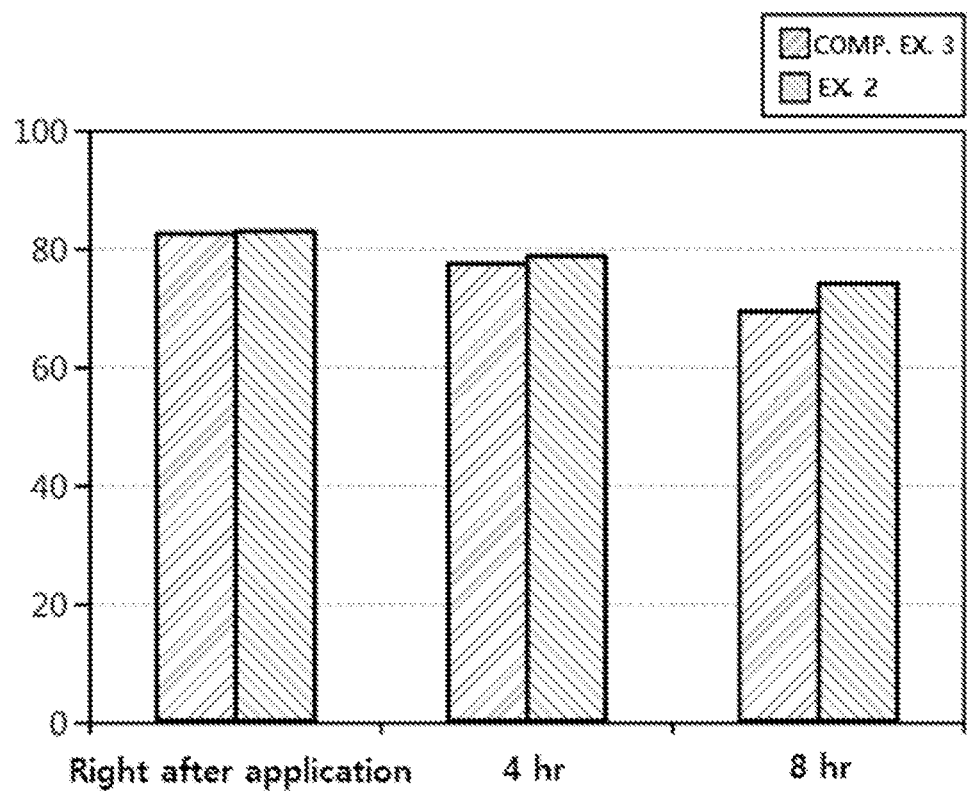
FIG. 4 is a graph illustrating the results of gloss of each of Comparative Example 3 and Example 2, as determined by using a glossmeter according to Test Example 3.

The results of gloss determination using a glossmeter are shown in FIG. 4, a decrease in gloss is shown in Table 5, and the results of sensory evaluation are shown in Table 6.

TABLE 5

| | Comp. Ex. 3 | Example 2 |
| --- | --- | --- |
| Decrease (4 hr) | 6.27 | 4.96 |
| Decrease (8 hr) | 16.02 | 10.12 |

TABLE 6

| | Comp. Ex. 3 | Example 2 |
| --- | --- | --- |
| Sustainability | 3.0 | 3.8 |
| Stuffy feel | 2.5 | 4.0 |

As can be seen from the results of FIG. 4 and Table 5, Comparative Example 3 including a larger amount of high-refractive index oil shows a similar level of initial gloss value as compared to Example 2 including an aqueous phase polyol and a smaller amount of high-refractive index oil, but shows a significant decrease in gloss with the lapse of time.

In addition, as can be seen from the results of evaluation of a feel of use in Table 6, Comparative 3 shows a lower score in terms of sustainability and a stuffy feel as compared to Example 2. It can be seen that the evaluation result of sustainability is similar to the tendency of the result of gloss determination, and a stuffy feel is increased as the content of high-refractive index oil is increased. This suggests that a large amount of high-refractive index oil causes a stuffy feel of use and degradation of sustainability, and the use of a high-refractive index polyol can reduce the content of high-refractive index oil to improve a stuffy feel and to assist maintenance of gloss.

Test Example 4: Water-In-Oil Type Makeup Cosmetic Formulation Depending on Content of High-Refractive Index Oil To determine the initial gloss and gloss-sustaining effect depending on the content of high-refractive index oil in a water-in-oil type cosmetic formulation including a high-refractive index polyol and an oil phase polymer, the following test was carried out.

TABLE 7

|  | Comp. Ex. 2 | Example 4 | Example 5 |
| --- | --- | --- | --- |
| Decrease (4 hr) | 10.45 | 4.57 | 9.54 |
| Decrease (8 hr) | 13.61 | 11.43 | 14.43 |

Figure 5:
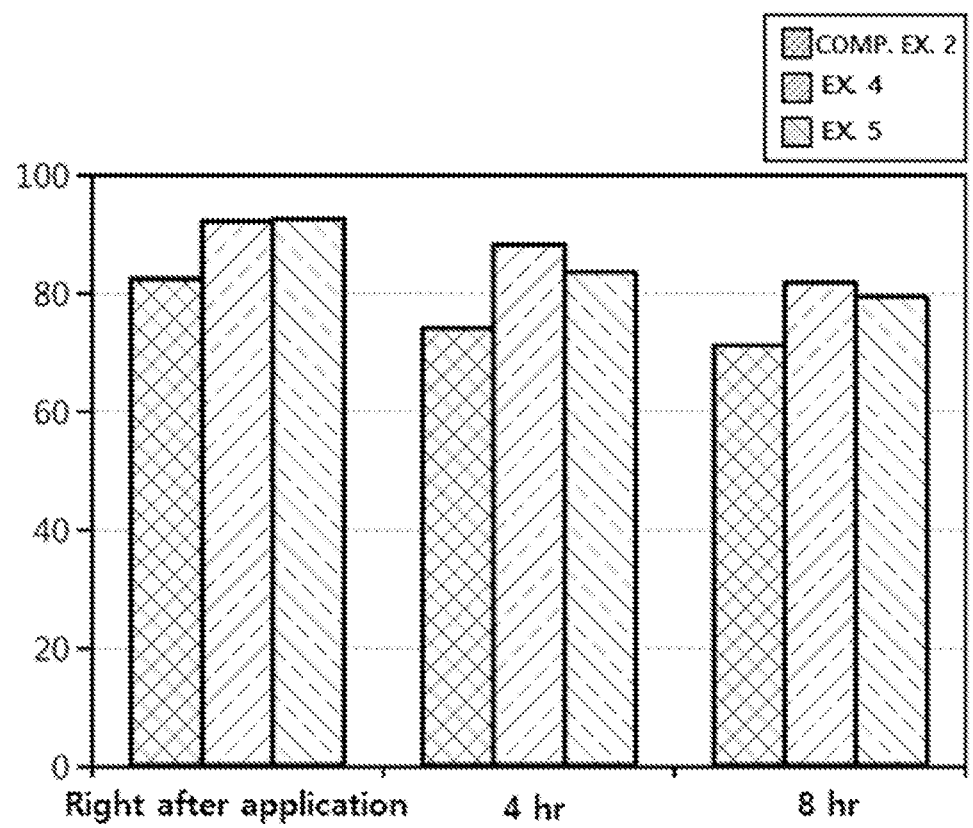
FIG. 5 is a graph illustrating the results of gloss of each of Comparative Example 2 and Examples 4 and 5, as determined by using a glossmeter according to Test Example 4.

As can be seen from the results of FIG. 5 and Table 7, Examples 4 and 5 including a high-refractive index polyol and an oil phase polymer and containing a smaller amount of high-refractive index oil shows a higher initial gloss value and a gloss value after the lapse of time, as compared to Comparative Example 2 merely including a larger amount of high-refractive index oil. Example 4 shows a smaller decrease in gloss with the lapse of time, as compared to Comparative Example 2. This suggests that when using high-refractive index oil, a high-refractive index polyol and an oil phase polymer at the same time, gloss sustainability can be improved.

In addition, Comparative Example 2 and Examples 4 and 5 were evaluated in terms of gloss sustainability and a stuffy feel of use in the same manner as Test Example 3.

TABLE 8

|  | Comp. Ex. 2 | Example 4 | Example 5 |
| --- | --- | --- | --- |
| Sustainability | 3.5 | 3.9 | 3.5 |
| Stuffy feel | 3.7 | 4.5 | 4.8 |

As can be seen from the results of Table 8, Examples 4 and 5 show a significantly high effect of improving a stuffy feel of use, while providing gloss sustainability equal to or higher than the gloss sustainability of Comparative Example 2.

What is claimed is:

1. A water-in-oil cosmetic composition for sustaining luster comprising: a high-refractive index oil, a high-refractive index polyol, and an oil phase polymer, wherein the high-refractive index oil has a refractive index (RI) of 1.44 or more, wherein the high-refractive index polyol has a refractive index (RI) of 1.39 or more, wherein the high-refractive index oil is used in an amount of 8-15 wt % based on the total weight of the composition, wherein the high-refractive index polyol is used in an amount of 10-20 wt % based on the total weight of the composition, wherein the oil phase polymer is present in an amount of 5-15 wt % based on the total weight of the composition, wherein the oil phase polymer is a silicone resin comprising trimethylsiloxy silicate, wherein the high-refractive index polyol is present in an internal phase, wherein the high-refractive index polyol is glycerin, wherein the high-refractive index oil comprises phenyl trimethicone and diphenylsiloxyphenyl trimethicone, and wherein the composition has a decrease in gloss of less than 5% over 4 hours.

2. A method for preparing a water-in-oil cosmetic composition for sustaining luster, including the steps of: (S1) agitating and dispersing each of an oil phase ingredient comprising a high-refractive index oil and an aqueous phase ingredient comprising a high-refractive index polyol; (S2) mixing the oil phase ingredient with a colorant and carrying out agitation; and (S3) adding the aqueous phase ingredient to the oil phase ingredient and carrying out emulsification, wherein the high-refractive index oil has a refractive index (RI) of 1.44 or more, wherein the high-refractive index polyol has a refractive index (RI) of 1.39 or more, wherein the high-refractive index oil is used in an amount of 8-15 wt % based on the total weight of the composition, wherein the high-refractive index polyol is used in an amount of 10-20 wt % based on the total weight of the composition, wherein the oil phase polymer is present in an amount of 5-15 wt % based on the total weight of the composition, wherein the oil phase polymer is a silicone resin comprising trimethylsiloxy silicate, wherein the high-refractive index polyol is glycerin, wherein the high-refractive index oil comprises phenyl trimethicone and diphenylsiloxyphenyl trimethicone, and wherein the composition has a decrease in gloss of less than 5% over 4 hours.

* * * * *